United States Patent [19]

Pieczenik

[11] Patent Number: 4,528,266
[45] Date of Patent: Jul. 9, 1985

[54] METHOD OF INSERTING UNIQUE DNA SEQUENCES INTO DNA VECTORS

[76] Inventor: George Pieczenik, 61 W. 62nd St., No. 11G, New York, N.Y. 10023

[21] Appl. No.: 428,538

[22] Filed: Sep. 30, 1982

Related U.S. Application Data

[62] Division of Ser. No. 80,668, Oct. 1, 1979, Pat. No. 4,359,535.

[51] Int. Cl.³ .................... C12Q 1/68; C12N 15/00; C12P 19/34
[52] U.S. Cl. ........................... 435/6; 435/91; 435/172.3; 935/24; 935/25; 935/27; 935/28; 935/29; 935/30; 935/31; 935/32; 935/77
[58] Field of Search ............... 435/6, 91, 172, 317; 935/29, 77

[56] References Cited

U.S. PATENT DOCUMENTS 4,237,224 12/1980 Cohen et al. ................. 435/172

OTHER PUBLICATIONS

Heffron et al., PNAS USA, vol. 75, pp. 6012–6016, Dec. 1978.
Maniatis et al., Cell, vol. 15, pp. 687–701, Oct. 1978.
Roberts et al., Crit. Rev. Biochem., vol. 4, p. 123 (1976).
Itakura et al., J. Biol. Chem., vol. 250, p. 4592 (1975).
Itakura et al., J. Am. Chem. Soc., vol. 97, p. 73227 (1975).
Scheller et al., Science, vol. 196, p. 177 (1977).
Sanger et al., PNAS USA, vol. 74, pp. 5463–5467 (1977).
Maxarn et al., PNAS USA, vol 74, pp. 560–564 (1977).
Sinsheimer, Ann. Rev. Biochem., vol. 46, p. 415 (1977).
Villa Komaroff et al., PNAS USA, vol. 75, pp. 3727–3731 (1978).
Bumell et al., Nature, vol. 279, p. 43 (1979).
Bolivar et al., Gene, vol. 2, p. 95 (1977).
Seeburg et al., Nature, vol. 270, p. 486 (1977).
Crick, Science, vol. 204, p. 264 (1979).
Pieczenik et al., J. Mol. Biol., vol. 90, p. 191 (1974).
Itakura et al., Science, vol. 198, pp. 1056–1063 (1977).
Polisky et al., PNAS USA, vol. 73, pp. 3900–3904, Nov. 1976.
Maricans et al., Nature, vol. 263, pp. 744–748 (1976).
Heyneke R et al., Nature, vol. 263, pp. 1313–1319 (1977).
Higuchi et al., PNAS USA, vol. 73, pp. 3146–3150 (1976).
Wu et al., Molecular Cloning of Recombinant DNA, Miami Winter Sympsoia, vol. 13, Edited by Scott et al., p. 244 (1977).

*Primary Examiner*—Alvin E. Tanenholtz
*Attorney, Agent, or Firm*—Roy D. Meredith

[57] ABSTRACT

Autonomously replicating DNA containing a unique nucleotide sequence, being an oligonucleotide of which its sequence does not otherwise exist in said DNA[inserted in a non-essential region thereof at a site not previously susceptible of restriction endonuclease cleavage].

5 Claims, No Drawings

METHOD OF INSERTING UNIQUE DNA SEQUENCES INTO DNA VECTORS

This is a division of application Ser. No. 080,668 filed Oct. 1, 1979, now U.S. Pat. No. 4,359,535.

INTRODUCTION

Recombinant DNA technology is a battery of techniques used to clone specific genes, construct DNA transfer vectors, and to manipulate genetic material isolated from a donor organism such that, upon transfer to a host organism, the donor genetic information may be expressed in the host. Fundamental to the practice of recombinant DNA technology is the existence of restriction endonucleases. These enzymes catalyze the hydrolysis of certain phosphodiester bonds of DNA, at specific sites as determined by a local sequence of nucleotides. Different restriction enzymes recognize different nucleotide sequences. The recognition sequences are randomly dispersed throughout the DNA of an organism. Shorter recognition sequences occur with higher frequency than longer ones. Due to the random distribution of restriction sites, the ability to cleave a DNA molecule at a desired locus, for excision of a segment of DNA or for insertion of a segment, is only possible when a restriction site is found at or near the desired locus. This limitation is a severe restriction on progress in the recombinant DNA field, since every new situation must be handled on an ad hoc basis, depending upon where the restriction sites are located in each case. Extensive mapping of restriction sites must be carried out to determine whether the desired insertions or excisions are feasible or to carry out nucleotide sequence analyses.

The present invention overcomes this major limitation by providing a general method for inserting restriction sites or other specific desired sequences into specific areas of a DNA transfer vector, virus, or other self-replicating entity. The term "autonomously replicating DNA element" is used herein to denote generically all such entities as plasmids, episomes, viral DNAs, mitochondrial and chloroplast DNAs and other extra-chromosonal DNAs, capable of being replicated within a living cell independently of the replication of the host cell chromosome DNA. The invention provides novel transfer vectors and a method for making such vectors as desired, for the safe replication of cloned genes, for nucleotide sequence analysis of cloned DNA segments, for expression of cloned genes under control of specific desired promoters, and for construction of DNA transfer vectors that serve as a library of genes carried thereon, specifically excisable at will. Further, the invention provides a method for simplified sequence determination without prior restriction mapping, and simplifies the location and identification of structural genes on cloned nucleotide sequences.

BACKGROUND AND PRIOR ART

The present invention builds upon an extensive body of prior art including the physical and chemical nature of nucleic acids, the principles of genetics and biochemistry, and on specific chemical and enzyme catalyzed reactions. The following is a non-exhaustive list of general background references useful for explaining operating principles and defining terms generally used in the art.

1. General

A. Watson, J. D., *The Molecular Biology of the Gene*, 3rd Ed., Benjamin, Menlo Park, Calif. (1976).

B. Hayes, W., *The Genetics of Bacteria and Their Viruses*, 2nd Ed., Blackwell Scientific Publ, Oxford (1968).

2. Restriction Endonucleases:

Roberts, R. J., *Crit. Rev. Biochem.* 4, 123 (1976).

3. Chemical Synthesis of Oligonucleotides:

a. Itakura, K., et al., *J. Biol. Chem.* 250, 4592, (1975).

b. Itakura, K., et al., *J. Am. Chem. Soc.* 97, 7327 (1975).

4. Restriction Site "Linkers":

Scheller, et al., *Science*, 196, 177 (1977).

5. Nucleotide Sequence Determination:

a. Sanger, F., et al., *Proc. Nat. Acad. Sci. USA*, 74, 5463 (1977).

b. Maxam, A. M., and Gilbert, W., *Proc. Nat. Acad. Sci. USA*, 74, 560 (1977).

6. DNA Replication:

Kornberg, A., *DNA Replication*,

7. Recombinant DNA:

a. Sinsheimer, R. L., *Ann. Rev. Biochem.*, 46 415 (1977).

b. Ullrich, A., et al., *Science*, 196, 1313 (1977).

c. Villa-Komaroff, L., et al., *Proc. Mat. Acad. Sci. USA*, 75, 3727 (1978).

d. Burrell, C. J., et al., *Nature*, 279, 43 (1979).

e. Bolivar, F., et al., *Gene*, 2, 95 (1977).

Developments in recombinant DNA technology have made it possible to isolate specific genes or portions thereof from higher organisms, such as man and other mammals, and to transfer the genes or fragments to a microorganism species, such as bacteria or yeast. The transferred gene is replicated and propagated as the transformed microorganism replicates. As a result, the transformed microorganism may become endowed with the capacity to make whatever protein the gene or fragment encodes, whether it be an enzyme, a hormone, an antigen or an antibody, or some portion thereof. The microorganism passes on this capability to its progeny, so that in effect, the transfer has resulted in a new strain, having the described capability. See, for example, Ullrich, A. et al., supra. and Seeburg, P. H., et al., *Nature*, 270, 486 (1977). A basic fact underlying the application of this technology for practical purposes is that DNA of all living organisms, from microbes to man, is chemically similar, being composed of the same four nucleotides. The significant differences lie in the sequences of these nucleotides in the polymeric DNA molecule. The nucleotide sequences are used to specify the amino acid sequences of proteins that comprise the organism. Although most of the proteins of different organisms differ from each other, the coding relationship between nucleotide sequence and amino acid sequence is fundamentally the same for all organisms. For example, the same nucleotide sequence which codes for the amino acid sequence of a human protein in human cells, will, when transferred to a microorganism, be recognized as coding for the same amino acid sequence, and may result in synthesis by the microorganism of the same human protein.

Abbreviations used herein are given in Table 1.

TABLE 1

| DNA | — | deoxyribonucleic acid | A | — | Adenine |
|---|---|---|---|---|---|
| RNA | — | ribonucleic acid | T | — | Thymine |
| cDNA | — | complementary DNA | G | — | Guanine |
| | | (enzymatically synthesized | C | — | cytosine |
| | | from an mRNA sequence) | U | — | Uracil |

TABLE 1-continued

| | | | |
|---|---|---|---|
| mRNA — messenger RNA | | ATP — | Adenosine triphosphate |
| dATP — deoxyadenosine triphosphate | | TTP — | thymidine triphosphate |
| dGTP — deoxyguanosine triphosphate | | | |
| dCTP — deoxycytidine triphosphate | | | |

The coding relationships between nucleotide sequence in DNA and amino acid sequence in protein are collectively known as the genetic code, shown in Table 2.

TABLE 2

| | Genetic Code | | | | |
|---|---|---|---|---|---|
| | U | C | A | G | |
| U | Phe | Ser | Tyr | Cys | U |
| | Phe | Ser | Tyr | Cys | C |
| | Leu | Ser | Non$^2$ | non$^3$ | A |
| | Leu | Ser | Non$^1$ | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

An important feature of the code, for present purposes, is the fact that each amino acid is specified by a trinucleotide sequence, also known as a nucleotide triplet. The phosphodiester bonds joining adjacent triplets are chemically indistinguishable from all other internucleotide bonds in DNA. Therefore the nucleotide sequence cannot be read to code for a unique amino acid sequence without additional information to determine the reading frame, which is the term used to denote the grouping of triplets used by the cell in decoding the genetic message.

Essential to recombinant DNA technology are the relatively small, autonomously replicating, DNA elements including plasmids and virus DNA molecules. These are used to infect, transfect, or transform host cells in which they are replicated. The process of uptake of such DNA by a living cell and replication in that cell is termed herein the transfer of such DNA to a host cell. The term "transfer" used herein, includes processes termed transformation, transfection or DNA uptake in the art. The genetic information contained in such molecules includes at a minimum that needed to insure the replication of the DNA after transfer to a host cell. Normally, these autonomously replicating elements carry additional genetic information. For example, plasmids often carry antibiotic resistence genes which confer survival value on host cells carrying the plasmids, and virus DNAs contain genes for virus coat proteins and for functions associated with maturation of intact viruses. In addition, wholly unrelated genes may be included. Autonomously replicating DNA elements exist as double stranded ring structures generally on the order of a few million daltons molecular weight, although some are greater than $10^8$ daltons in molecular weight. They usually represent only a small fraction of the total DNA of a host cell. The DNA is usually separable from host cell DNA by virtue of a great difference in size between them. In addition, they are usually isolated as intact ring structures, whose topological constraints may be exploited to product separations on the basis of density, from host cell DNA which is typically isolated in the form of linear fragments. Many such DNAs may be induced to carry a segment of heterologous DNA by technique of opening the ring, inserting the fragment of heterologous DNA and reclosing the ring, forming an enlarged molecule comprising the inserted heterologous DNA segment. Alternatively, a segment of heterologous DNA may be inserted in place of a previously deleted non-essential region. In either situation, the DNA then serves as a carrier for the heterologous inserted fragment and is termed a transfer vector.

Transfer may be accomplished by any process whereby host cells are induced to incorporate the DNA into the cells. Although the mechanics of the process remain obscure, it is a widely observed phenomenon, known to occur in many species of bacteria, yeast, and cultured mammalian cells. Once a cell has incorporated a transfer vecter, the latter is replicated within the cell and the replicas are distributed to the daughter cell when the cell divids. Any genetic information contained in the nucleotide sequence on the transfer vector DNA can, in principle, be expressed in the host cell. Typically, a transformed host cell is recognized by its acquisition of traits carried on the plasmid, such as resistence to antibiotics. Any given transfer vector may be made in quantity by growing a pure culture of cells containing the transfer vector and isolating transfer vector DNA therefrom.

The means for insertion of heterologous DNA segments into transfer vector DNA includes the restriction endonucleases. Restriction endonucleases are hydrolytic enzymes capable of catalyzing site-specific cleavage of DNA molecules. The locus of restriction endonuclease action is determined by the existence of a specific nucleotide sequence. Such a sequence is termed the recognition site for the restriction endonuclease. Many restriction endonucleases from a variety of bacterial species have been isolated and characterized in terms of the nucleotide sequence of their recognition sites. Some restriction endonucleases hydrolyze the phosphodiester bonds on both strands at the same point, producing blunt ends. Others catalyze hydrolysis of bonds separated by a few nucleotides from each other, producing free single stranded regions at each end of the cleaved molecule. Such single stranded ends are self-complementary, hence cohesive, and may be used to rejoin the hydrolyzed DNA. Since any DNA susceptible of cleavage by such an enzyme must contain the same recognition site, the same cohesive ends will be produced, so that it is possible to join heterologous sequences of DNA which have been treated with restriction endonuclease to other sequences similarly treated. See Roberts, R. J., supra.

Restriction sites are relatively rare, those having short recognition sequences being more commonly encountered than those having longer recognition sequences. An important feature of the distribution of restriction endonuclease recognition sites is the fact that they are randomly distributed with respect to structural genes and with respect to reading frames. In the prior art, there is no known way to predict, (a) whether a given restriction site will exist in a given region and (b) where within a given region they will be located. Consequently, a major initial effort of all prior art recombinant DNA projects involves the construction of a restriction map, which is a diagram of the DNA under investigation, showing the relative locations of various restriction sites. Once the restriction map is known, it is then possible to devise the optimum strategy for inserting and deleting fragments, approximately as desired. An important consequence of the random distribution of restriction sites is that the investigator must devise essentially ad hoc strategies for each project, utilizing the nature and location of restriction sites as best he can for his purposes. An exception to this general statement is that individual restriction sites may be deleted by known techniques. DNA which has been cleaved by restriction endonuclease may be rejoined in a reaction catalyzed by the enzyme DNA ligase. Fragments having cohesive ends are covalently joined with high efficiency under conditions conducive to base pairing of the cohesive ends. The enzyme also catalyzes the joining of fragments having base-paired, blunt ends. However, fragments having protruding single stranded non-complementry ends are not joined.

The term "expression" is used in recognition of the fact that an organism seldom if ever makes use of all its genetically endowed capabilities at any given time. Even in relatively simple organisms such as bacteria, many proteins which the cell is capable of synthesizing are not synthesized, although they may be synthesized under appropriate environmental conditions. When the protein product, coded by a given gene, is synthesized by the organism, the gene is said to be expressed. If the protein product is not made, the gene is not expressed. Normally, the expression of genes in *E. coli* is regulated as described generally, infra, in such manner that proteins whose function is not useful in a given environment are not synthesized and metabolic energy is conserved.

The development of capabilities for synthesizing DNA chemically (See Itakura, et al, supra) has made it possible to synthesize restriction enzyme recognition site sequences, Scheller, et al, supra. A desired oligonucleotide recognition site sequence may be chemically synthesized, attached to the ends of a DNA fragment by blunt end ligation, treated with the appropriate restriction endonuclease, to provide cohesive ends, then inserted in a transfer vector cleaved by the same restriction endonuclease, whereby the cut ends of the transfer vector DNA and of the heterologous fragment are cohesive and may be joined together with high efficiency in a ligase catalyzed reaction.

The organization of structural genes coding for individual amino acid sequences within the total genome is a matter of much current interest. It appears that the genome of virtually all organisms, with the exception of certain viruses, consists of both essential and nonessential regions. These terms are functionally defined and depend upon the growth conditions. For example, the ampicillin resistance gene is not essential for growth of bacteria in a medium lacking ampicillin; it is essential if ampicillin is in the medium. In addition to specific structural genes whose essentiality depends upon conditions, there appear to exist regions which are non-coding in the conventional sense, whose presence is not essential. In prior art genetic analyses, such regions have been identified by deletion mutations in which segments of the genome are permanently excised without loss of viability. An example is the b2 of lambdaphage. In eucaryotes there are untranslated regions to be found on either side of most structural genes. In addition, current evidence indicates that the structural genes in some instances contain internal non-coding regions, terms introns, whose function is at present unknown. (See Crick, F. *Science* 204, 264 (1979)).

The concept of essential and non-essential genes is fundamental to the present invention. For purposes of this application, a gene of an autonomously replicating DNA element is essential if, under the growth conditions employed, the function for which it codes is required for continued replication of the element. A region which is non-essential, with reference to a given autonomously replicating element, is one whose function is not required, under the growth conditions, for continued replication of the element. It will be understood that a given region may be defined as essential under one set of growth conditions and non-essential under another. A case in point is the ampicillin resistance gene previously described. A gene which is essential under one set of conditions may be rendered non-essential by complementation. In complementation, the function of a gene provided by one genetic element is duplicated by providing a second gene within the cell, coding for the same function. If the first should be defective, bearing an insertion, deletion or base change leading to loss of function, the growth and replication of the DNA element is still permitted by providing a normal function from the second gene. Therefore, by manipulation of growth conditions and/or complementing functions, it is possible to render virtually any gene essential or non-essential.

Nucleotide sequence analysis of DNA has proven to be a powerful technique for the elucidation of gene structure and for the prediction of amino acid sequences. The methods of Maxam and Gilbert, supra, and of Sanger, supra, provide powerful tools for rapid sequence analysis. Both methods are presently limited by the need to have detailed restriction mapping of the DNA to be sequenced. This is so because both sequencing methods employ gel electrophoresis for the separation of the oliognucleotides. The length of sequences which can be determined from a given starting point are limited by the resolution of the electrophoresis gels. In order to extend the sequence beyond the nucleotide length resolvable by current gels, it is necessary to provide, by means of restriction endonuclease cuts, new starting points for the analysis procedure. Although the sequence procedures themselves are rapid, getting sufficient information about restriction sites is relatively time consuming. Furthermore, as with other aspects of recombinant DNA technology, all experiments must be designed on an ad hoc basis, depending upon what restriction sites exist and how they are located with respect to each other, in the DNA to be sequenced. Prior to the present invention, no general method has existed for undertaking routine sequence analysis of DNA fragments.

GENERAL DESCRIPTION OF THE INVENTION

The present invention provides, for the first time, a general method for introducing specific restriction sites in a desired region of a genome. The technology of recombinant DNA is thereby freed of a major restraint, with consequences that are far reaching, as will be described infra.

The invention is applicable to any autonomously replicating DNA element that can be introduced into a host cell and replicated therein. Such DNA elements include plasmids, bacteriophages, and animal or plant viruses, with or without inserted heterologous sequences. The DNA element must comprise, as a condition of operability, either zero or one restriction site sequence for a given restriction enzyme. For many applications of the invention, the sequence need not be a restriction site sequence, but merely any sequence not otherwise found in that DNA. A unique sequence is defined as one which does not exist in the DNA of a given autonomously replicating element, unless inserted or generated by techniques described herein. As a practical matter, the use of restriction site sequences makes it easy to define unique sequences since the DNA will not be cut by a given restriction enzyme if its recognition sequence is missing. Most commonly, the sequence will be one of the relatively long recognition sequences such as PstI, EcoR1, or HindIII. If the DNA element bears a single restriction site, it can be deleted by techniques known in the art (Polisky, B. et al, *Proc. Nat. Acad. Sci. U.S.A.*, 73, 3900 (1976), so that the general technique is applicable with sites of either 0 or 1 frequency.

The DNA of the autonomously replicating element is usually isolated as a double stranded circular DNA. After purification, the DNA is then randomly cleaved to give linear double stranded DNA. The procedure will yield a population of linear DNA molecules having circularly permuted sequences. It will be understood that any DNA that is directly isolatable as circularly permuted linear sequences will be operative in the invention, although DNA molecules having natural terminal redundancies will not. In practice, it is unnecessary to achieve truly random cutting of the circular DNA. Indeed, it is unlikely that truly random cleavage can be achieved experimentally, since most DNA molecules contain areas of secondary structure which may be subject to cleavage at a lower rate than other areas of the same DNA molecule. As long as the cleavage is quasi-random, and occurs without systematic bias throughout the genome, the method of the present invention will be operative. Any method for introducing random double-strand cleavage of circular DNA, is suitable for the present invention.

After the cleavage steps, a synthetic oligonucleotide bearing a unique nucleotide sequence, is attached to both ends of the linear molecules by blunt end ligation. The molecules are then treated with the restriction endonuclease specific to the inserted sequence, to generate cohesive ends on the linear molecules. The molecules are then converted back to circles with the aid of DNA ligase under conditions promoting base pairing at the cohesive ends.

At all stages of the procedures described herein, circular and linear forms of DNA having the same molecular weight are readily separated by known fractionation techniques. In most instances, the circular form is necessary to infect or transform host cells.

The circular DNA bearing the random inserted unique sequence is transferred to a suitable host cell by appropriate means including transformation, transfection, or infection. Host cells bearing and replicating the treated DNA are then grown under defined conditions. Replication of the inserted DNA in the host and the production of progeny DNA or progeny virus, will only occur where there has been an insertion of the unique sequence in a non-essential region of the genome. The locus of the insert is therefore defined operationally. Individual clones bearing the insert at a specific locus may then be isolated for further study and analysis.

The process described above may be repeated as often as desired, with the same or with different inserts. Several cycles of random cutting, insertion and selection, and cloning, will generate a multiple insert restriction vector (MIRV). When the MIRV is generated using normal growth conditions, the normally essential functions of the DNA will be bracketed by inserted sequences in virtually all of the non-essential regions. On the other hand, by complementing for a specific function, it is possible to isolate clones having inserts within a specific desired function. Therefore, the invention makes it possible to introduce restriction site sequences either around functional genes or within functional genes, simply by varying the growth and selection conditions. The progress is based upon the basic concept of genotypic selection which involves evolutionary constraints acting at the nucleotide level, see Pieczenik, G., *Congressional Record,* 95th Cong., No. 24, pp. 323–340 (1977).

There are far reaching consequences which follow from the ability to construct transfer vectors and other autonomously replicating DNA elements having restriction sites located in desired areas of the sequence. These include:

(1) The construction of a safe transfer vector for maintaining and replicating cloned genes of heterologous origin. A restriction site for inserting cloned DNA, or for cloning DNA from a heterogeneous mixture, may be generated to lie within a non-essential region of a transfer vector such that the heterologous region is not expressed.

(2) Sequencing vectors can be designed. Such vectors would be capable of receiving heterologous inserted DNA which, being inserted at a non-essential site, would not interfere with normal replication of the vector. The vector is then used to conduct sequence analysis by the primer method, as described by Sanger et al, supra. As will be described in detail, infra, the present invention may be used to provide two restriction sites in tandem, one of which is employed for the insertion of the heterologous gene and the other is employed for priming the sequence analysis.

(3) Expression transfer vectors may be generated by placing the insert sequence within an expressed gene. When the reading frame is maintained, a heterologous sequence will be translated from the promoter of the expressed gene, resulting in a fusion protein, according to techniques known in the art.

(4) A virus or transfer vector which has been treated with multiple inserts such that the inserts bracket the essential genes will serve as libraries for those specific genes. A specific gene may be withdrawn, or excised, by treatment with the set of restriction enzymes whose sites bracket the desired gene.

(5) The invention provides a rapid method for sequencing any autonomously replicating DNA element. In this case, a multiplicity of randomly inserted sites will provide convenient unique priming loci for initiating the sequence priming reactions. By this means, the complete sequence of a virus or transfer vector could be obtained without resort to detailed restriction mapping.

(6) The invention provides a way of mapping the essential and non-essential regions of any autonomously replicating DNA element, without reference to the nature or function of the essential regions. This mapping technique is termed "genotypic mapping" herein.

SPECIFIC EMBODIMENTS OF THE INVENTION

The basic invention is generally applicable to any autonomously replicating DNA element transferable to host cells and replicatable therein. The examples which follow are merely illustrative of the manner of making specific products of the invention and applying specific methods of the invention. Unless it is desired to provide a cleavage site, the sequence to be inserted need not be a restriction site sequence, but need only be a sequence not found in the DNA. In general, such a sequence may be operationally defined as a short oligonucleotide which does not hybridize with the DNA under conditions where hybridization of complementary oligonucleotides of the same length would occur. Where it is desired to insert a restriction site sequence, the invention is not limited to unique sequences. The process may also be carried out where there exists a single restriction site sequence in the DNA. In this case, the sequence may be deleted or altered, often without loss of function. Conditions for transformation and growth will vary with the host organism, as a matter of ordinary skill in the art. Further variations and modifications of technique may be appropriate, as matters of ordinary skill, to adapt the basic invention to specific circumstances.

EXAMPLE 1

Random Insertion of Unique Sequences

The system employed herein is the bacteriophage f1 and its host, *Escherichia coli* K38. The viral DNA of f1 phage is single stranded, however, a double stranded replicating form (RF) may be isolated from infected host cells under conditions of inhibited protein synthesis. The f1 RF is not cut by restriction enzyme PstI EcorR1 or HindIII and therefore lacks the sequences 5'-CTGCAG-3', 5'-GAATTC-3', and 5'-AAGCTT-3', respectively. Closed circular f1 RF DNA is isolated by a modification of the method of Pieczenik, G, et al., *J. Mol. Biol.* 90, 191 (1974).

Growth of *E. coli* K38-Two liters of super broth (tryptone, 32.0 gm; yeast extract, 20.0 gm NaCl, 5.0 gm, 6N NaOH, 2.3 ml up to 1 liter, pH 7.4, sterilized) are distributed into 6- 1 liter flasks and sterilized. They are inoculated from an overnight growth, (6 ml). K38 is a male strain, restriction K+, modification K+, and supressor minus, high frequency male donor C, received from Zinder (Lyons and Zinder, (ref.) 1972).

The cultures are incubated at 37° C. with constant swirling. The bacterial growth is monitered periodically by reading the O.D. at 700 nm on a colorimeter. The culture is diluted at an O.D. 1.0 (or monitored O.D. of 0.2) for infection. This corresponds to a cell density of about $4.5 \times 10^8$ cells/ml. (B) Infection with f1 Bacteriophage cells are infected at a high multiplicity of infection and after initial adsorption, protein synthesis is blocked in order to accumulate RF rather than single stranded phage. 0.1 ml of f1 virus at aitre of $1.2 \times 10^{14}$/ml is added to each of the six flasks. The cultures are swirled gently at 37° C. for 15 minutes at which time chloramphenicol is added directly or 12.5 ml of a 0.75 mg/ml solution (dissolved in Ethanol/Water, 1/20 per volume) to each flask. Cultures are then shaken vigorously for another hour. The bacteria are pelleted by centrifugation at 10K RPM at 4° C. for 20 minutes in a high speed centrifuge. The pellets are then washed with cold buffer (140 mM NaCl, 20 mM TrisHCl, pH 7.3). The cells are recentrifuged and resuspended in a total of 40 ml of the above solution. Approximately 5 mg of egg white lysozyme is added, the solution brought up to pH8.0, and incubated at 37° C. for 30 minutes. The cells are then osmotically shocked with 80 ml of ice-water and 10 ml of 5% sodium dodecyl sulfate (SDS) (electrophoretic purity). The mixture is shaken until clear, Triton X-100[1] (1%) can replace the SDS. This avoids getting rid of the SDS, as many enzymes are active in Triton X100. One third volume of 4M NaCl is added and shaken. The solution should be clear and viscous if proper lysis has taken place.

[1]Trademark, Rohm and Haas, Nutly, N.J.

Chromosomal DNA removal and de-proteinization—The solution after having settled at 4° C. for several hours is spun for 3 hours at 21K RPM at 4° C. on a high speed centrifuge. For smaller volumes, 1 hour at 34K RPM on an ultra high speed centrifuge is effective in getting rid of most of the bacterial DNA. The supernantant is then dialyzed for three hours against 4 liters of buffer (20 mM Tris pH 8.0, 1.0 mMEDTA) to remove SDS. This is unnecessary if Triton X-100 is used. The phenol for extraction of protein is prepared from equilibrated phenol with 10 mM Tris pH 7.8, 1.0 mMEDTA and 0.02M sodium Tetraborate to bring the pH up over 7. There is an alternative procedure that does not equilibrate the phenol. One can add sodium acetate pH 5.5 to the phenol and deproteinize with the acidified phenol. The aqueous layer is separated from the phenol layer by centrifugation at 3K RPM for 15 min. for the neutral phenol extraction and 9K RPM for 30 minutes for the acidic phenol extraction. The acidic phenol extraction brings down alot of the chromosomal DNA still in solution.

Rnase digestion and proteinase K digestion The phenol extraction will give three layers. The top layer is removed, with an inverted tip pasteur pepette, and acidified with 0.5 volumes of sodium acetate (2M) pH 5.0 and then precipitated with 2 volumes of isopropanol, at −20° C. overnight, or in any dry ice—isopropanol bath for 1 hour. The nucleic acid will come out of solution as a white flock and can be spun. For deproteinization one does not need to re-acidify with sodium acetate before precipitation). The precipitate is resuspended in 10 ml of TSE (50 mM NaCl, 5 mM EDTA, and 50 mM Tris, pH 7.8). This is re-acidified with sodium acetate and re-precipitated with cold ethanol, at −20° C. The precipitate is then washed with 75% ethanol to remove any remaining SDS (omit when using Triton X-100, in small preps). The precipitate is air dried and resuspended in 10 ml of TSE and RNAse A (pancreatic) added to a final concentration of 50 ug/ml. The RNAse A is preheated for 15 minutes at 80° C. to kill any DNAse activity. Incubation for RNAse treatment is at 37° C. for 30 minutes. The RNAse A and other nucleases are then digested with the addition of proteinase K up to 0.5 mg/ml final concentration for 30 minutes at 37° C. The DNA is then re-acidified with sodium acetate and re-precipitated with 2.5 volumes of cold 95% ethanol, at −20° C., for several hours. For small preparations the RNAse treatment can be eliminated.

CsCl density centrifugation The precipitate is isolated by centrifuging at 3K RPM for 30 minutes at 4° C. This is air dried and resuspended in 5 ml of Buffer (10 mM NaCl, 1 mMEDTA 10 mM Tris pH 8.0). The optical absorbance is then determined at 260 and 280 nm. The ratio (260/280) should be around 2.0. If not, re-precipitate or extract with ether to eliminate phenol. A DNA solution having a maximum of O.D. of 15 260 nm should be made up to 3.3 ml. This is added to 4.0 gm of CsCl and 0.75 ml of 0.7 mg/ml ethidium bromide. The ethidium bromide concentration is important as it intercalates with the supercoiled RFI and shifts its density away from nicked RF and Chromosomal DNA. The tubes are centrifuged on an ultrahigh speed centrifuge at 34K RPM, 18° C., for 48–72 hours on a SW 27 or 24 hours on a sorvail vertical rotor.[2] The lower band, which can be visualized with short or long wave ultraviolet light (long is preferable, less nicking of DNA), is the RFI-fI DNA. Sometimes, on long runs RFII separates from the Chromosomal band. RFII is nicked at one unique site.

[2] DuPont Instruments, Wilmington, Del.

The RFI band is removed and the ethidium bromide is eluted by an isopropanol solution saturated with CsCl (20 g CsCl, 20 ml water, 40 ml isopropanol). This extraction is repeated several times. The CsCl is dialyzed from the DNA at 4° C. for 12 hours with 2 liters of buffer (10 mm NaCl, 1 mm EDTA, 10 mM TRIS pH 7.8). The RFI is precipitated by adding 0.05 volumes 2M sodium acetate, pH 5.0, and 3 volumes cold 95% ethanol, −20° C. overnight.

The RFI is pelleted by centrifugation is siliconized Corex[3] tubes at 10K RPM for 30 minutes at 4° C. The precipitate is air dried and then resuspended in 0.1 tris pH 7.4, 1M EDTA to a concentration 25.0 O.D. (260) ml of 1 ug/ul.

[3] Trademark, Corning Glass Works, Ithaca, N.Y.

There are three methods to randomly introduce nicks into supercoiled RFI, or other double stranded circular DNA. 1. Let it sit on a frost free freezer for two months (this converts over 50%) of RFI and RFII by introducing single-stranded breaks (nicks). The Frost-free freezer cycle freezes and thaws the DNA solution.

2. Freeze-thaw the DNA solution at least twenty times (can convert over 90% of RFI to randomly nicked RFII.

b 3. A more uniform method is to digest the RFI with DNAse I solution 1 mg/ml in distilled water, stored at −20° C., at an enzyme to DNA ratio of 1/500 by weight. The reaction buffer contains 10 mM tris pH 7.6, 10.0 mM MgCl$_2$, 10.0 mM dithiothreitol, 100 mM NaCl, in distilled water, stored at −20° C. at an enzyme to DNA ratio of 1/500. The reaction buffer contains 10 mm tris PH 7.6, 10.0 mm MgC12, 10.0 mm dithiothreitol, 100 mm NaCl. The reaction is monitored over time on an agarose slab gel (1% by weight agarose 40 mM Tris Acetate, pH 7.2, 20.0 mM sodium acetate, 2.0 mM EDTA, and visualized by soaking in a 0.5 ug/ml solution of ethidium bromide by long wave length (366 nm) ultraviolet light. The RFII moves slower than RFI. When conversion is greater than 98%, as monitored by the gel, then the DNAse is removed by phenol, ether extraction, and chromatography on a sephadex G-100 column[4] (pre-equilibrated, pre-boiled in 5 mM Tris pH 7.4 1 mM EDTA). The void column is collected (the second 0.2 ml on a 1 ml plastic pipette column). This is dessicated and resuspended to 25.0 O.D. (260) ml in 0.01 Tris pH 7.4, 1 mM EDTA. The RFII is re-run on the 1% agarose gel with RFI which migrates fater than RFI, and a HindII restriction cut of RFI and RFII (HindII, 1 unit/ug RF), 2 hours at 37° C., in 10 mM Tris pH 7.9, 6.6 mM MgCl$_2$, 1 mM dithiothreitol, 60 mM NaCl). The RF has one HindII restriction site and therefore the incubation generated duplex linear RFIII. RFIII moves between RFI and II on 1% agarose gel electrophoresis.

[4] Trademark, Pharmacia, Inc., Uppsala, Sweden.

There are three ways to convert randomly nicked RFII to terminally random RFIII, generally applicable to any circular DNA.

1. Freeze-thaw and monitor conversion of gel.
2. Treat RFII with 0.2N NaOH at 37° C. for several hours and monitor conversion on gel.
3. If randomly nicked RFII is treated with DNA polymerase I and one of the deoxynucleotide triphosphates, e.g., 40 uM dATP, and appropriate buffer (See DNAse 1 buffer above), the DNA polymerase 3' to 5' exonuclease activity will take over and the enzyme will nibble from the nick on the RFII on the back to the first A residue, leaving a short single-stranded region on the circular duplex molecule.

The resulting single stranded region will be about 3 nucleotides long on the average. The reaction can be stopped with 1 ul of 0.2M EDTA. The polymerase can be removed by extracting with phenol, and with ether, and chromatographing a sephadex G-100 column, (Pharmacia), Lypholizing, resuspending, and reprecipitating from ethanol (as described in detail) supra. The DNA is treated with S1 nuclease under mild conditions. Nicked RFII polymnerase-treated DNA 100 ug, is digested with 100 units of S1 nuclease in 30 mM sodium acetate pH 4.6, 50 mM NaCl, 1 mm ZnSO$_4$, for 5 minutes to two hours, for conversion to RFIII. The S1 nuclease is removed in the same manner as described for removal of polymerase. The DNA is now a linear DNA duplex with 1–4 nucleotides of sticky end, depending on how the S1 cut the exposed single strand. This sticky end can be filled in by adding polymerase 1, the four deoxynucleoside triphosphates, 40 uM each and polymerase buffer (same as DNAse 1 buffer, supra). The DNA polymerase is removed from the DNA as given above. The DNA RFIII is monitored on 1% agarose gel as above. It should be over 90% RFIII.

The RFIII DNA may or may not have 3' hydroxyl and 5' phosphate groups. The freeze-that methods do not guarantee this, nor does the S1 nuclease. Therefore, removing all phosphate end groups with bacterial alkaline phosphatase and then adding 5' phosphate from gamma labeled ATP with polynucleotide kinase will guarantee that the duplex DNA has proper 5' phosphates and 3' hydroxyls.

A unique sequence of ten nucleotides is prepared for insertion into f1-DNA by chemical synthesis. The sequence to be synthesized is TTCTGCAGAA. This sequence is self-complementary and contains a Pst 1 recognition site. The HindIII site on a fragment CCAAGCTTGG is commercially available from Collaborative Research, Beverly, Mass.

Ligation is done under conditions (as above) with a molar ration of 10 insertion sequences to one RFIII. Ligation results in attachment of insertion sequence at both ends of the terminally random RFIII. This is repurified from the fragment by either phenol, ether, G-100 (as above) or by sucrose gradient sedimentation. After extensive dialysis and reprecipitation from ETOH, it is digested with Pst 1 endonuclease. Digestion conditions are 20 mM Tris (pH 7.5, 10 mM MgCl$_2$, 50 mM (NH$_4$)$_2$SO$_4$, 100 ug/ml bovine serum albumin at 30° C. Pst 1 endonuclease is somewhat unstable at 37° C. This digestion generates cohesive Pst 1 ends (4 nucleotides).

The cohesive-ended RFIII is repurified and religated at low dilution to favor intra-molecular ligation giving the closed circular RFI with the insertion sequence regenerated but randomly (or quasi-randomly inserted in the RFI sequence). The ring closure reaction can be monitored on an agarose gel as above.

EXAMPLE 2

Screening for Single Insert Vector (SIV)

Transfection will be done as a variation of the procedure of Taketo, Hayashi, and Kuno (ref) (1972). *E. coli* K38 is first made competent for transfection, by treatment with $CaCl_2$. An overnight culture of K38 is inoculated into 100 mls of superbroth (Example 1). Cells are grown to mid log phase Cells are added to ½ volume $CaCl_2$ (0.05M) at 0.C. for 15 minutes. The cells are then concentrated at 2K RPM at 4° C. for 20 minutes, the resuspended in 0.05M $CaCl_2$ to an equivalent O.D. at 660 nM of 10.0. DNA to be transfected (RFI containing the insertion sequence) and RFI (as control) are placed in sterile siliconized tubes on ice, and 0.1 ml of $CaCl_2$ treated cells are added. After 10 minute incubation, the tubes placed in an incubator for at least 2.5 minutes at 37° C. 1 ml. of ice cold 0.05M $CaCl_2$ is added and the mixture placed on ice. 1 ml of the mixture is then placed in molten soft Agar at 45° C. After about 15 seconds the mixture is placed on bottom agar. After plates solidify they are incubated overnight at 37° C. Plates are then screened for plaques. Formation of plaques will generally indicate transfection by an RF having the insertion sequence in a non-essential region.

Breeder reactions can also be started. These 10 ml of superbroth inoculated with the K38 transfected with the RFI carrying the insertion sequence. If the single plaques do not contain bacteriophage with the insertion sequence, only a few, the breeder can be used to make an RFI DNA preparation as above. This RFI DNA will be a mixed population with some DNA containing the insertion sequence. By recutting with Pst 1, this RFI DNA preparation will be divided into RFI DNA and RFIII (duplex linear with Pst 1 ends). These are separated by sucrose gradient or CsSl ethidium bromide. The RFIII is religated and used for transfection. This procedure allows one to select biochemically for the DNA molecules containing the insertion sequence and therefore to enhance for them.

Bacteriophage f1 plaques whose DNA contains the insertion sequence can be screened in several ways:

1. Filter hybridization—The phage will be replica plated with toothpicks on marked grids. Duplicate plates will be made. One set of the duplicates are transferred to Millipore filters.[5] Millipore filters (HAWP 304FB or GSWP 304 F0) are cut to petri dish size. The filters are placed on the plates for 10 minutes at 40° C. They are removed gently and floated on 1.0N NaOH, 1.5M NaCl for 10 minutes, and then transferred to 0.2M Tris, 1.0M NaCl pH 7.4 for 30 seconds. They are washed in 6×SSCP (0.6M NaCl, 0.75M sodium citrate, 0.065M $KH_2PO_4$ 0.005M disodium EDTA for 20 seconds. They are baked in a vacuum oven (wrapped in foil) at 80° C. for 2 hour. The filters then are washed for one hour in 5×SSCP 65° C. washed one hour in 5×SSCP and D buffer (0.6M NaCl, 0.0075M sodium citrate, 0.065 $KH_2PO_4$, 0.005M disodium, Ficail 400, 0.2%, polyvinyl pyrrolidone —40, 0.2% bovine serum albumin, 0.2% DNA, 50 ug/ml, SDS 0.1%) at 65° C. The labelled probe, which will be the insertion sequence made radioactive by addition of ($^{32}P$) using DNA kinase or polymerase I in a nick-translation reaction, will be added to the filters which are in a polyethylene bag with D buffer. The bag is sealed and placed at 65° C. for 18 hours. The filters are then washed 6× for 30 minutes in D buffer, then for 60 minutes in 1×SSC-D buffer at 65° C., and at room temperature in 5×SSCP. The filters are then subjected to autoradiography. The labelled plaques contain the phage with sequences that are complementary and therefore identical to the insertion sequence. This procedure allows one to fix the denatured phage DNA on a filter and do in situ hybridization to localize the screen the bacteriophage. Positive plaques are then diluted, plated and screened again. This procedure should allow screening several hundred plaques a day.

[5] Millipore Corporation, Bedford, Mass.

Mini-RF preparation: Depending on the efficiency of ligation and transfection and if one has already transfected from a breeder RF preparation, one can screen individual rapid RF preparations as above. 10 ml cultures of single plaque infections yield enough RF1 to screen on a mini-agarose gel system (described above). The conversion of RF1 to linear RFIII is distinctive and does not require either RNAse treatment of CsCl. It requires a lysis, spin, rapid acid phenol, and ethanol precipitation. 10 colonies can be screened a day. This technique has the advantage that if any RFIII is formed from cutting with Pst 1 one can retransfect with the DNA to increase the chance of finding phase with inserts.

EXAMPLE 3

Generation of HindIII or EcoR1 Sites Adjacent to a Pst I Insert

The logic behind this screening method is as follows: The insertion sequence is TTCTGCAGAA. It contains a Pst I Site (CTGCAG). If this site is inserted adjacent to GAA it will generate GAATTC which is an EcoR1 site. The chance of this happening in this orientation is 1/64 if the insertion is random (assuming equimolar base composition). Because this can also insert near a TTC on its 3' side, TTCTGCAGAATTC, this also generated an EcoR1 site. Therefore the chance of generating an EcoR1 site is 1/32. This can be used to screen for the statistics of insertion. The same test can be applied to HindIII. If the insertion sequence inserts adjacent to AAGC, it generates AAGCTTCTGCAGAA which contains a HindIII site.

The procedural strategy to isolate these vectors is to take a phage stock containing the Pst 1 insertion fragment and grow a mixed culture. Isolate the RF1 (as above, but with 3 CsCl gradients) and restrict the RF1 preparation with EcoR1 or HindIII exonuclease. Some of the RF1 will contain these sites and will generate RFIII or duplex linears. The RFIII can be separated from the RF 1 on an ethidium bromide CsCl gradient. The RFIII is religated and transfected This will generate plaques which contain EcoR1 sites or HindIII sites adjacent to the Pst 1 site.

EXAMPLE 4

Sequencing Vector—Derived from MIRV

One half of the plaques containing the EcoR1 site or the HindIII (depending which enzyme was used to generate the duplex linear) will have the site 5' to the modified Pst 1 insertion sequence. The plaques in this configuration can be used as sequencing vectors for the Sanger-Coulson Dideoxy sequencing method with the insertion sequence fragment as primer. Any EcoR1 or HindIII or Sma 1 fragment can can be sequenced by inserting into this vector, without having to isolate restriction fragments. By inserting the fragment to be sequenced, by inserting it in the vector and transfecting, one needs to only pick plaques and isolate the single stranded DNA (as above) and prime with the insertion sequence oligonucleotide. One-half of the plaques will give sequence in the newly inserted fragment, one-half will give f1 sequence. This is because one can insert the insertion sequence and generate EcoR1 or HindIII sites on either side with equal frequency. So one needs to screen by sequencing to make sure one picks the vectors containing the newly generated site on the 5' side of the insert rather than the 3' side. Once one has developed these vectors, one can keep adding insertion sites of different specificities for f1 of sites that do not exist in the wild-type f1. This is done by taking the sequencing vector and putting in a HindIII and later a Sma 1 sequence in the manner used to put in the original modified Pst 1 sequence. One selects by converting from Rf1 to RFIII and back to RF1 and transfecting. The selection procedure is biochemical and genotypic. By inserting only one site per molecule, one can screen by converting the supercoiled duplex to the linear duplex. The linear duplex can be separated from the supercoiled duplex by a CsCl ethidium bromide gradient or by gel electrophoresis. The linear can be converting back to the supercoiled duplex by ligation and this can be transfected to generate phage containing this site in various locations. This is a very powerful and quick genotypic selection procedure. It does not require functional product for selection. The foregoing method can be employed for mapping non-essential regions of the DNA. This mapping technique is termed genotypic mapping.

The f1 RF DNA modified to contain a Pst 1 site with an EcoR1 site newly generated on the 3' side of the Pst I site inserted in an area of the genome capable of accepting large DNA sequences is useful as a sequencing vector. Heterologous DNA to be sequenced is treated to attach EcoR1 linker sequences to either end and inserted into the EcoR1 site of the sequencing vector. The heterologous insert is precisely located with respect to a unique Pst I site. The oligonucleotide sequence that was inserted to generate the Pst I site may also be used as a primer for the sequencing reactions of the Sanger method, as described supra. The sequence of the vector itself in the region of the EcoR1 site will be known in advance, in order to define the sequence boundaries of the inserted heterologous region. The length of the heterologous region which may be sequenced from a single priming site is limited only by the resolution of the gel systems used for separating the oligonucleotides.

EXAMPLE 5

Nucleotide Sequence Analysis without Prior Restriction Mapping

The complete sequence of any autonomously replicating DNA element may be determined simply by providing that the inserted sequence is distributed about the genome at a frequency comparable to the resolving power of gels used to separate oligonucleotides generated by the sequencing reaction. With currently available techniques, the limit of resolution is 300 to 400 nucleotides in length and future improvements made it likely that fragments over 1,000 nucleotides will be resolvable in the future. The frequency with which inserted fragments are distributed may be increased by providing complementation for the essential functions or providing growth conditions in which essential functions are rendered non-essential. Individual clones from the random insertion process may be used with the insert as primer to generate sequence directly in the 3' side of the inserted sequence. A family of such sequences will provide regions of overlap which will define the order of the sequences. Given a reasonably uniform distribution of insertion sites, a virus or transfer vector of having approximately 3,000 nucleotides should yield a complete sequence from the analysis of about 15 clones. Longer sequences, or more complete confirmation, can be obtained by analyzing a larger number of clones. It should be noted that the foregoing sequence technique does not require that the inserted sequence be a restriction sequence, since no restricting cutting is involved. The entire sequence may be determined without reference to a restriction site and without the necessity of restriction mapping.

EXAMPLE 6

Multiple Insertion Restriction Vector (MIRV)

A MIRV is generated by reiterations of the fundamental process for the insertion of previously nonexistent restriction sites into a transfer vector or virus DNA. A MIRV may be constructed so as to have multiple insertions of the same restriction site or to have a multiplicity of unique restriction sites. As a consequence of predetermined growth and selection conditions, a MIRV can contain a sufficient number of restriction sites located between essential regions, to be used in effect as a library for the genes it contains. A given gene may be excised by treatment of the MIRV with a specific combination of restriction enzymes that will liberate the desired gene. In this way, each gene of the MIRV may be separately isolated for sequence analysis or for transfer to other genetic elements. Conversely, a MIRV is useful as a depository for several different genes on the same vector, each having a separate address on the transfer vector.

As examples of the above uses, a polyoma virus MIRV is useful as a source for the individual genes of the virus. In this way, each gene of polyoma virus may be studied separately, without knowledge of or reference to its function. Similarly, a transfer vector MIRV may be constructed into which each of the essential regions of the polyoma may be inserted, so that all essential functions are carried on a single transfer vector, but separated from one another in non-expressed regions of the transfer vector, for enhanced safety.

Supercoiled polyoma virus DNA is prepared from cultured mouse 3T6 cells by differential salt precipitation and CsCl ethidium bromide equilibrium density centrifugation, essentially as described in Example 1. Randomly cut linear duplex DNA is prepared from supercoiled polyoma DNA by the methods described in Example 1 for converting f1 RF1 DNA to RFIII DNA. Unique restriction site sequence suitable for insertion are previously determined by screening experiments to detect susceptibility to a battery of restriction enzymes. Oligonucleatide sequences corresponding to each such sequence found with zero frequency in polyoma DNA are synthesized. Each of several sequences is introduced in turn, in a population of random cut linear double stranded DNA molecules, by iterations of the procedure described in Example 1, including the steps of attaching the oligonucleotide sequence to be inserted on the ends of random cut linear DNA's, reclosing the ring, transfecting susceptible cells, in this case mouse 3T6 cells, isolating viable clones evidenced by the ability to form a plaque, amplifying the amount of cloned DNA by introducing a cycle of growth in susceptible cells, reisolating supercoiled circular DNA and again preparing random cut linear DNA for insertion of the next oligonucleotide. After several such cycles, insertion sites will saturate the non-essential sites of the virus, so that it will be possible to specifically and individually excise individual essential regions, for sequence analysis, structural studies and functional studies in model systems, without any prior knowledge of the functions or map locations of the essential functions. The polyoma virus MIRV also serves as a source of useful sequence information, using the sequencing method of Example 4.

EXAMPLE 7

The Inserts Generated Within Genes

The technique for generating the insertion of unique oligonucleotide sequences within specific genes simply involves manipulating the growth conditions such that the target region for receiving an insert is functionally non-essential. In practice this means either manipulation of the growth conditions by providing a particular nutrient or removing a potential inhibitor, or providing complementation for the essential function. The former technique will be effective for generating inserts in the ampicillan resistance gene of pB322, for example. Transformed cells containing inserts in the ampicillan resistance gene will be tetracycline resistant but ampicillan sensitive. Colonies of cells growing on agar plates containing tetracycline will be transformed cells, and colonies which do not replicate onto ampicillan containing plates contain inserts in the ampicillan resistance gene.

In the case of bacteriophage f1, oligonucleotide insertion into expressed regions is accomplished by transfecting cells previously infected with wild type or mutant f1 capable of complementing the target function. In general, mutant complementation is preferred in order to reduce the frequency of occurrence of plaques from cells not transfected by insert containing DNA. Such plaques will however, contain mixtures of the complementing mutant and insert containing phage. The DNA of the latter can be separated by treatment with the restriction enzyme corresponding to the inserted sequence, physically separating double stranded linear DNA thereby produced from the circular DNA of the complementing phage, the reclosing the circles with DNA ligase.

In general, two complementing strains having their mutations in two separate genes will be the minimum required to permit the insertion of oligonucleotide sequences throughout the genome, with the exception of true cis-acting genes such as the replication origin. In general, any technique for providing conditions of non-essentially for a given region will enable the insertion of oligonucleotide segments into that region. Such methods are well known to those of ordinary skill in the art.

The combination of techniques for insertion into essential and non-essential regions, as defined herein, makes possible construction of a MIRV comprising a library of subfunctions. Such sub-functions include ribosome binding sites, promoters, attenuators, splicing sequences, sequences coding for precursor portions of proteins and functional domains within proteins, i.e., active sites, or antigenic determinants. The subfunctions are individually isolatable and may then be used as building blocks for construction of vectors having desired properties.

EXAMPLE 8

Sequencing large inserts in a single sequencing vector

The technique for random insertion of restriction sites in a circular DNA, such as mitochondrial DNA, can be exploited to provide the sequence of the entire circular DNA using a sequencing vector as described in Example 3. As with previously described sequencing techniques herein, knowledge of the restriction map of mitochondrial DNA is unnecessary.

In the following embodiment of the invention, a large segment of DNA is inserted at an insertion site on a sequencing vector or expression vector as described in Example 1. It is anticipated that structural restraints will prevent the acceptance of large inserts at all sites where oligonucleotide inserts could exist. Therefore it will be necessary to select for those vectors which permit insertion of large sequences. The location of the areas capable of accepting long insert sequences will provide a map of the structural apexes or of regions where large discontinuities interfere with viability. Vectors stable to large inserts must be separately selected for sequencing such large inserts. The selection process provides a structural map of the vector.

The circular mitochondrial DNA is converted to randomly terminal duplex linear DNA essentially as described in Example 1. The modified Pst I site described in Example 1 is then blunt-end ligated to the ends of the linear molecules, treated with Pst 1 endonuclease and inserted into the modified Pst 1 containing f1 sequencing vector described in Example 3. *E. coli* K38 cells are transfected and DNA preparations are made from individual plaque isolates. The oligonucleotide sequence is then used to prime the synthesis of complementary oligonucleotide strands as described by Sanger et al supra. In this method, the replication of the sequencing vector depends only on f1 bacteriaphage functions. All functions of the DNA to be sequenced, mitochondrial DNA in the present example, are operationally non-essential, since the only essential genes are those required for replication of the vector. Consequently insertions of the Pst 1 oligonucleotide sequence in the mitochondrial DNA will be randomly distributed. Each sequence segment, determined by priming from an individual plaque isolate, will be different. By picking a sufficient number of plaques, the entire sequence is determined. The average number of plaque isolates needed to determine the sequence is root the total sequence length divided by the resolution of the gel plus the sequence root of that value times three. Given a resolution of 200 nucleotides per gel, a sequence 20,000 nucleotides in length should be 99% covered with overlapping sequences by picking 100 plaques plus 30 (3 times the square route of 100). The sequence is confirmed by internal consistency of the overlapping sequences and may be further confirmed by restriction maps.

CONCLUDING REMARKS

It can be seen from the foregoing general description of the invention and from the specific examples illustrating applications thereof, that the invention has manifold and far reaching consequences. The invention basically provides novel treated DNA molecules and a method of treating DNA molecules to obtain the product molecules themselves. The fundamental product of the invention is a population linear DNA molecule comprising permutations of the same nucleotide sequence and having a unique oligonucleotide sequence attached at both ends. The attached sequence is unique in the sense that it is found nowhere else in the linear molecule. Subsequent manipulations, selection techniques, growth conditions, cleavage methods, and sequencing methods all contributes to providing end uses for such modified DNA molecules that vastly extend the scope and power of recombinant DNA technology by providing restriction site sequences either in essential or non-essential regions, as desired, and by providing improved and simplified nucleotide sequencing techniques.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of inserting a unique oligonucleotide sequence into a non-essential region of an autonomously replicating DNA element, comprising,
    isolating double stranded circular molecules of the DNA, each having the same nucleotide sequence,
    cleaving the circular DNA at random with respect to nucleotide sequence, producing a population of linear, double stranded DNA molecules comprising circular permutations of the same nucleotide sequence,
    joining a unique oligonucleotide sequence to the ends of the linear DNA molecules, said unique oligonucleotide sequence not otherwise existing in said DNA element, then
    rejoining the ends to form circular double stranded DNA molecules having the oligonucleotide of unique sequence inserted at random with respect to the nucleotide sequence of each circular DNA molecule,
    transferring the circular DNA having said unique insert sequence to a host organism under conditions permitting replication of the DNA, and
    selecting for progeny of the circular DNA having a unique insert sequence, said progeny bearing said insert in a non-essential region of the DNA.

2. A method of making a population of linear DNA molecules having the same nucleotide sequence circularly permuted and having a unique oligonucleotide sequence covalently attached at the ends thereof, said unique oligonucleotide sequence not otherwise existing in said DNA molecules comprising:
    (a) isolating circular DNA of an autonomously replicating DNA element,
    (b) cutting the circular DNA at random, thereby generating a population of linear DNA molecules having the same nucleotide sequence circularly permuted, and
    (c) covalently attaching said unique oligonucleotide sequence to the ends of the linear DNA molecules of step (b).

3. A method of making a modified autonomously replicating DNA element wherein the modification comprises a unique oligonucleotide sequence not otherwise existing in said DNA element, said sequence inserted randomly with respect to the nucleotide sequence of said DNA element, comprising the steps of:
    (a) isolating and purifying circular DNA of an autonomously replicating DNA element,
    (b) cutting the circular DNA at random, thereby generating a population of linear DNA molecules having the same nucleotide sequence circularly permuted,
    (c) covalently attaching said unique oligonucleotide sequence to the ends of the linear DNA molecules of step (b),
    (d) covalently attaching the ends of the linear DNA molecules intramolecularly, whereby circular DNA molecules containing said unique oligonucleotide sequence inserted randomly with respect to nucleotide sequence is made.

4. The method of claim 1 wherein the unique oligonucleotide sequence is inserted into a structural gene of the autonomously replicating DNA element by providing growth conditions for a host organism such that the structural gene for receiving the insert is functionally non-essential, whereby the circular DNA having said unique sequence in said structural gene is transferred to said host organism under conditions permitting replication of the DNA.

5. The method of genotypically mapping an automatically replicating DNA element comprising the steps of:
    (a) providing a population of linear DNA molecules of said DNA element, comprising circular permutations of the same nucleotide sequence,
    (b) attaching a unique oligonucleotide sequence to the ends of the linear DNA molecules of step (a), said unique sequence not otherwise existing in said DNA element,
    (c) rejoining the ends of the linear molecules of step (b), thereby forming a population of circular autonomously replicating DNA molecules having said unique oligonucleotide sequence inserted randomly with respect to the nucleotide sequence,
    (d) transforming or transfecting a population of host cells with the population of circular DNA molecules resulting from step (c),
    (e) isolating clones of the DNA molecules of step (c), said clones having the unique oligonucleotide sequence inserted in a non-essential region of the autonomously replicating DNA element, under preselected growth conditions, and
    (f) measuring the relative positions of the unique oligonucleotide sequence inserts of individual clones, with respect to the nucleotide sequence of the DNA element, thereby mapping the nonessential regions of its genome, under the preselected growth conditions, without reference to or knowledge of the function of any gene therein, said mapping being genotypic.

* * * * *